United States Patent [19]

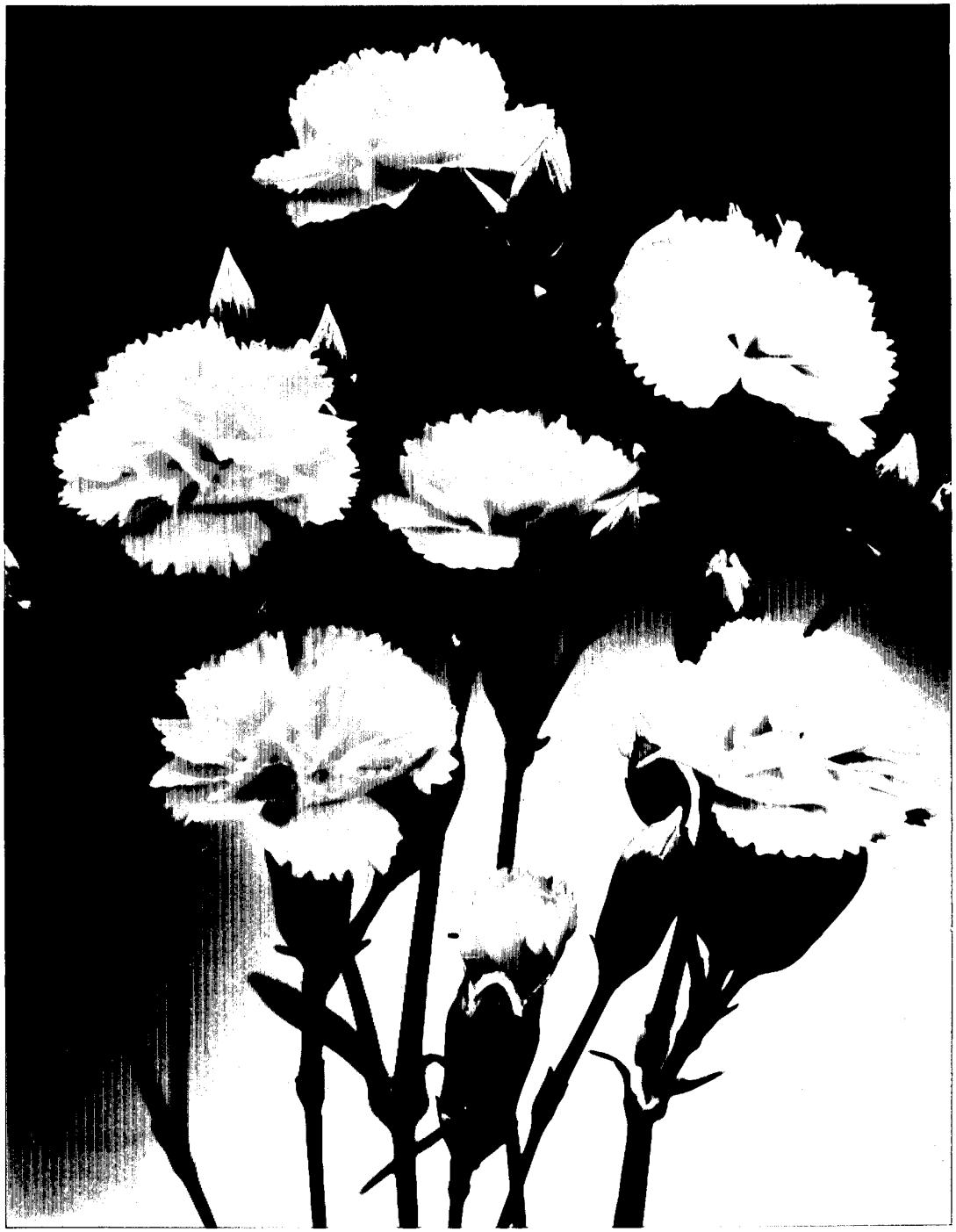

van Andel

[11] Patent Number: Plant 5,565

[45] Date of Patent: Oct. 1, 1985

[54] CARNATION NAMED STANOCT

[75] Inventor: Jacob van Andel, Aalsmeer, Netherlands

[73] Assignee: B. V. Handelskwekerij/M. C. van Staaveren, Aalsmeer, Netherlands

[21] Appl. No.: 556,263

[22] Filed: Nov. 30, 1983

[51] Int. Cl.[4] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new carnation cultivar distinguished by its relatively small blooms of red-purple coloration which are produced continuously, Spring and Fall, on long, strong flowering stems having an upright growth habit with abundant foliage.

1 Drawing Figure

BACKGROUND OF THE NEW PLANT

This new carnation cultivar originated as a seedling resulting from my crossing at Aalsmeer, Holland, of selected carnation varieties from my collection maintained at Aalsmeer for breeding purposes. This particular plant was selected by me for propagation and test because of the bright red coloring of its relatively small blooms and apparently strong and vigorous growth habit. This seedling was propagated by me at Aalsmeer by means of cuttings from the parent plant and the results of that propagation were so favorable that propagation by means of cuttings was carried on at Aalsmeer through several successive generations, which demonstrated that the distinguishing characteristics of this plant were retained from generation to generation and appeared to be firmly fixed.

DESCRIPTION OF THE DRAWING

This new carnation cultivar is illustrated by the accompanying full color photographic drawing which shows flowers and buds in various stages of opening as they appear on several flowering stems, the color rendition being as nearly true as it is possible to obtain by conventional commercial photographic procedures.

DESCRIPTION OF THE NEW PLANT

The following is a detailed description of my new carnation cultivar based upon observations of plants grown in greenhouse at Aalsmeer, Holland, in the Summer of 1983, the color designations being according to The R.H.S. Colour Chart published by The Royal Horticultural Society of London, England.

THE PLANT

Origin: Seedling.
Parentage:
- *Seed parent.*—Unnamed seedling #06-2G (unpatented).
- *Pollen parent.*—"Stacero" (unpatented).

Classification:
- *Botanic.*—*Dianthus caryophyllus.*
- *Commercial.*—Greenhouse carnation.

Form: Tall bush.
Height: Average.
Growth: Strong and upright with normal branching.
Foliage:

- *Quantity.*—Abundant.
- *Number of leaves.*—Depending on season.
- *Size of leaf.*—Medium.
- *Shape of leaf.*—Oblong.
- *Texture.*—Smooth.
- *Color.*—Upper side — Blue/Green with waxy layer. Under side — Blue/Green with waxy layer.

THE BUD

Size: Small.
- *Diameter.*—About 10 mm.
- *Length.*—About 30 mm.

Shape: Ovoid and pointed becoming generally cylindrical at time of opening.
Rate of opening: Normal.
Sepals: Hooded over bud and stand up when flowers open.
- *Color.*—Inside — Grey/green with dark purple top end. Outside — Grey/green.

Calyx:
- *Shape.*—Funnel shaped.
- *Size.*—Medium.
- *Splitting.*—Rarely.
- *Aspect.*—Smooth.

Peduncle: Rigid and erect.
- *Color.*—Dark green.

THE FLOWER

Blooming habit: Continuous Spring and Fall.
Size of bloom: Small.
- *Diameter.*—About 40 mm.
- *Depth.*—About 20 mm.

Borne: Raceme.
Shape: High centered.
Petalage:
- *Number of petals.*—From 30 to 40.
- *Arrangement.*—Generally imbricated.
- *Shape of petals.*—Fan shaped with dentate margins.
- *Texture.*—Soft.
- *Appearance.*—Shiny.
- *Color.*—Outer and inside petals for all seasons: Upper side: Body — 60D. Base — Grey/green. Reverse side — R.H.S. 60D.

Flower stem:
- *Length.*—Depending on season.
- *Color.*—Dark green.
- *Character.*—Strong and upright.

Persistence: The petals hand on and dry.
Disease resistance: *Fusarium oxysporum* as observed at Aalsmeer, Holland.
Lasting quality:
*On plant.*—20 Days.
*As cut flower.*—10 To 14 days.

REPRODUCTIVE ORGANS

Stamens: Of medium number.
*Anthers.*—Size: Medium. Color: Cream.
*Filaments.*—Length: Medium. Color: Cream/pink.

*Pollen.*—Color: Yellow.
Pistils:
*Number.*—One.
*Style.*—Length: Medium. Color: Pink.

I claim:

1. A new and distinct carnation cultivar, substantially as herein shown and described, characterized by its continuous production of bright red/purple blossoms of small size borne singly on rigid, erect pedicels.

* * * * *